US006716960B2

(12) United States Patent
Alnemri et al.

(10) Patent No.: US 6,716,960 B2
(45) Date of Patent: Apr. 6, 2004

(54) MCH3, A NOVEL APOPTOTIC PROTEASE, NUCLEIC ACIDS ENCODING AND METHODS OF USE

(75) Inventors: Emad S. Alnemri, Ambler, PA (US); Teresa Fernandes-Alnemri, Ambler, PA (US); Gerald Litwack, Bryn Mawr, PA (US); Robert Armstrong, San Diego, CA (US); Kevin Tomaselli, San Diego, CA (US)

(73) Assignees: Idun Pharmaceuticals, Inc., San Diego, CA (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 10/337,060

(22) Filed: Jan. 2, 2003

(65) Prior Publication Data

US 2003/0119169 A1 Jun. 26, 2003

Related U.S. Application Data

(62) Division of application No. 09/944,851, filed on Aug. 31, 2001, now abandoned, which is a continuation of application No. 08/556,627, filed on Nov. 13, 1995, now Pat. No. 6,462,175.

(51) Int. Cl.$^7$ .......................... C07K 16/40; C07K 16/00
(52) U.S. Cl. .............................. 530/288.26; 530/387.9; 530/389.1
(58) Field of Search .................. 530/387.9, 288.26, 530/389.1

(56) References Cited

U.S. PATENT DOCUMENTS 6,087,150 A    7/2000  He et al.
6,462,175 B1 * 10/2002  Alnemri et al.

FOREIGN PATENT DOCUMENTS

WO    WO 96/13603    5/1996

OTHER PUBLICATIONS

Alnemri et al., "Cloning and Expression of Four Novel Isoforms of Human Interleukin–1β Converting Enzyme with Different Apoptotic Activities," *The Journal of Biological Chemistry* 270(9): 4312–4317, Mar. 3, 1995.
Barinaga, M., "Cell Suicide: By ICE, Not Fire," *Science 26*: 754–756, 1994.
Black et al., "Activation of Interleukin–1β by a Co–induced Protease," *FEBS Letters 247*: 386–390, 1989.
Cerretti et al., "Molecular Cloning of the Interleukin–1β Converting Enzyme," *Science 256*: 97–100, 1992.
Duan et al., "ICE–LAP3, A Novel Mammalian Homologue of the *Caenorhabditis elegans* Cell Death Protein Ced–3 Is Activated during Fas– and Tumor Necrosis Factor–induced Apoptosis," *J. Biol. Chem. 271*(3): 1621–1625, 1996.
Enari et al., "Involvement of an ICE–like protease in Fas–mediated apoptosis," *Nature 375*: 78–81, 1995.

Fernandes–Alnemri et al., "Mch3, a Novel Human Apoptotic Cysteine Protease Highly Releated to CPP32," *Cancer Research* 55(24): 6045–6052, 1995.
Fernandes–Alnemri et al., "In vitro activation of CPP32 and Mch3 by Mch4, a novel human apoptotic cysteine protease containing two FADD–like domains," *Proceedings of the National Academy of Sciences of the United States of America* 93(15): 7464–7469, 1996.
Fernandes–Alnemri et al., "CPP32, a novel human apoptotic protein with homology to *Caenorhabditis elegans* cell death protein Ced–3 and mammalian Interleukin–1 beta– converting enzyme," *Journal of Biological Chemistry* 269(49): 30761–30764, Dec. 9, 1994.
Gagliardini et al., "Prevention of Vertebrate Neuronal Death by the *crmA* Gene," *Science 263*: 826–828, 1994.
Henkart, P., "Ice family protease: Mediators of all apoptotic cell death?," *Immunity 4*: 195–201, Mar. 1996.
Howard et al., "IL–1–Converting Enzyme Requires Aspartic Acid Residues for Processing of the IL–1β Precursor at Two Distinct Sites and Does Not Cleave 31–kDa IL–1a," *Journal of Immunology 147*: 2964–2969, 1991.
Korsmeyer, S.J., "Regulators of cell death," *TIG 11*(3): 101–105, 1995.
Kostura et al., "Identification of a Monocyte Specific Pre–interleukin 1β Convertase Activity," *Proceedings of the National Academy of Science USA 86*: 5227–5231, 1989.
Kumar et al., "Induction of Apoptosis by the Mouse Nedd2 Gene, Which Encodes a Protein Similar to the Product of the *Caenorhabditis elegans* Cell Death Gene ced–3 and the Mammalian IL–1β–converting Enzyme," *Genes Development 8*: 1613–1626, 1994.
Lippke et al., "Identification and Characterization of CPP32–Mch2 Homolog 1, a Novel Cysteine Protease Similar to CPP32," *Journal of Biological Chemistry 271*(4): 1825–1828, 1996.
Los et al., "Requirement of an ICE/CED–3 protease for Fas/APO–1–mediated apoptosis," *Nature 375*: 81–83, 1995.
Miura et al., "Induction of Apoptosis in Fibroblasts by IL–1β–Converting Enzyme, a Mammalian Homolog of the *C. elegans* Cell Death Gene ced–3," *Cell 75*: 653–660, 1993.
Nagata and Golstein, "The Fas Death Factor," *Science 267*: 1449–1456, 1995.

(List continued on next page.)

*Primary Examiner*—Christina Chan
*Assistant Examiner*—Maher Haddad
(74) *Attorney, Agent, or Firm*—Seed Intellectual Property Law Group PLLC

(57) ABSTRACT

The invention provides an isolated gene encoding Mch3, or functional fragment thereof. Also provided is an isolated nucleic acid sequence encoding Mch3 or functional fragment thereof. The gene or nucleic acid sequence can be single or double stranded nucleic acids corresponding to coding or non-coding strands of the Mch3 nucleotide sequence. An isolated Mch3 polypeptide or functional fragment thereof is also provided.

3 Claims, 5 Drawing Sheets

OTHER PUBLICATIONS

Nicholson et al., "Identification and inhibition of the ICE/CED–3 protease necessary for mammalian apoptosis," *Nature 376*: 37–43, 1995.

Pai et al., "Purification and cDNA cloning of a second apoptosis–related cysteine protease that cleaves and activates sterol regulatory element binding proteins," *Proceedings of the National Academy of Sciences of the United States of America 93*(11): 5437–5442, 1996.

Ray et al., "Viral Inhibition of Inflammation: Cowpox Virus Encodes an Inhibitor of the Interleukin–1β Converting Enzyme," *Cell 69*: 597–604, 1992.

Reed, J.C., "Mini–Review: Cellular Mechanisms of Disease Series; Bcl–2 and the Regulation of Programmed Cell Death," *Journal of Cellular Biology 124*: 1–6, 1994.

Sleath et al., "Substrate Specificity of the Protease That Processes Human Interleukin–1β," *Journal of Biological Chemistry 265*: 14526–14528, 1990.

Steller, H., "Mechanisms and Genes of Cellular Suicide," *Science 267*: 1445–1449, 1995.

Tewari et al., "Yama/CPP32beta, a mammalian homolog CED–3, is a CrmA–inhibitable protease that cleaves the death substrate poly(ADP–ribose) polymerase," *Cell 81*: 801–809, 1995.

Thompson, C.B., "Apoptosis in the Pathogenesis and Treatment of Disease," *Science 267*: 1456–1462, 1995.

Thornberry et al., "A Novel Heterodimeric Cysteine Protease is Required for Interleukin–1β Process in Monocytes," *Nature 356*: 768–774, 1992.

Tiso et al., "Chromosomal Localization of the Human Genes, CPP32, Mch2, Mch3, and Ich–1, Involved in cellular Apoptosis," *Biochemical and Biophysical Research Communications 225*(3): 983–989, 1996.

Walker et al., "Crystal Structure of the Cysteine Protease Interleukin–1β–Converting Enzyme: A $(p20/p10)_2$ Homodimer," *Cell 78*: 343–352, 1994.

Wang et al., "*Ich–1,* an *Ice/ced*–3–Related Gene, Encodes Both Positive and Negative Regulators of Programmed Cell Death," *Cell 78*: 739–750, 1994.

Williams and Smith, "Molecular Regulation of Apoptosis: Genetic Controls on Cell Death," *Cell 74*: 777–779, 1993.

Wilson et al., "Structure and Mechanism of Interleukin–1β Converting Enzyme," *Nature 370*: 270–275, 1994.

Yuan et al., "The *C. elegans* Cell Death Gene ced–3 Encodes a Protein Similar to Mammalian Interleukin–1β–Converting Enzyme," *Cell 75*: 641–652, 1993.

Bendayan M., "Possibilities of False Immunocytochemical Results Generated by the Use of Monoclonal Antibodies: the Example of the Anti–Proinsulin Antibody," *J. Histochem. Cytochem 43*(9):881–886, Sep. 1995.

Bost et al., "Antibodies Against a Peptide Sequence within the HIV Envelope Protein Crossreacts with Human Interleukin–2," *Immunol. Invest. 17*(6–7):577–586, Aug.–Oct. 1988.

* cited by examiner

Fig. 1A

```
                                                                            R  S  P  G  R  G  S  W  F  V  Q  A  L  C  S  I  L  E  E  H  G  K  D  L  E  I  M  Q  I  L  T  R  V  N  D  R  V  A  R  H  272
GGAGGAGCCCAGGAGGAAGAGGCTCCTGGTTTGTGCAAGCCCTCTGCTCCTCATCCTGGAGGAGCACGGAAAAGACCTGGAAATCATGCAGATCCTCACCAGGGTGAATGACAGAGTTGCCAGGC  857
  G  A  Q  E  E  A  P  G  L  C  K  P  S  A  P  S  W  R  S  T  E  K  T  W  K  S  C  R  S  S  P  G  *                             253
                                                                                                                                  303
  F  E  S  Q  D  D  P  H  F  E  K  K  Q  I  P  C  V  V  S  M  L  T  K  E  L  Y  F  S  Q  *
ACTTTGAGTCTCAGTCTGATGACCCACACTTCGAGAAGAAGCAGATCCCCTGTGGTCTCCATGCTCACCAAGGAACTCTACTTCAGTCAGTAACCATATCAGGGGTACATTCTAG             977
CTGAGAAGCAATGGGTCACTCATTAATGAATCACATTTTCTCTGAATTTTCAGAACTTTCAGGAAGCTCTAATTCAGGAAGAACTTAATTCAACAGGGAAGAAACTTTC                   1097
TGGTGCTGTGCTTTGTTCCTTTGTCTCTGAATTTTCAGAGACTTTTCATTTGGTGACTGTGAATCAATGTGTACTTCATTGGTGACTGTGTAACAGTGGTAGAGTCATGTTGCCAAAAGAATCCAATGTTTTGAC  1217
GACTTAATACATGCAACAGAAGTGACTTCTGGAGAAGCTCTGTGTCCAATGGCTGTGTGTCCACTGGTAGTGGTAACAGTGGTATTGAGTGTATTGATGATTTTCATTAGGCAGATTTTCATGCCAAAGAATCCAATGTTTGAC  1337
AAAACACAGCCAAGGGATATTTACTGACTTCTGTCTCTTTATTGCAGAATGTGATCAGATTCTGATATGTATCCATAGAAGCTTAATGATTCTGATATGTATCCACCACACACCCAGT          1457
GAGGAGAAAAAGCTTAATGATTCTGATATGTATCCACCACACACCCAGTGTTCACAGAGATTTAATACAGGAAAATTGACTTACATAGATGA                                    1577
TAAAGAGAAGAAGCCAAACAGAAGACTTAGGAGTTAGGAGTATCCAGTCTATGGGATCATCCAGAGGAGTTTGGTTCCTGTGTCCAGTAGTGGAGAGGAGCTCAGTAGTGCTGAACCATGGTG     1697
GGGGCTGCTAGTGGGAGTCCCTCACCAGCACCTTCCACCAGCACCTTCCACCAGCACCTTCCGAAGCCACCTCACCAAGGACCTTGGAAGAGCAAGGACCAAGGACCAAGGACCAAGGAAATGGATG  1817
CTATCCTGCCCTCACACATCTCCACCAGACACATAAGTAATCACTGAACACTTTTCAATTAATCACTCAATTCATTCAGATGATATGTGTAAAACAATCTGTTTTGGCT                   1937
TAAGCCTGGCCCATAATGTGAACATAAGCTTAAAATCTGTTATAGCTTTAAAAATCTGTTATAGCTTTTCAAGATATAATATCGTGTCAATCAATCAATATTAACCACATAATGTGTGTAACATCTGTTATATCTCC  2057
TTATGTGCAAAATCTGTTATTGTTTTCAAGATGTTTTCAAGATGGTGTATCTTTGATAAATGACTGTTTTTTCTGCCTAATAGTAACTGGTTAAAAAACAAATGTTCATATTTATTGATTAAAA    2188
AAGATTTTTGGCACTTTGTTTCAAGATGGTGTATCTTTGATAATCTTTGATTCTTTTGAATTCTTTGATAAATGACTGTTTTTTTCGCCTAATAGTAACTGGTTAAAAAACAAATGTTCATATTTATTGATTAAAA  2297
ATGTGGTTGCTT  2309
```

Fig. 1B

SEQUENCE LISTING

<160> NUMBER OF SEQ ID NOS: 17

<210> SEQ ID NO 1
<211> LENGTH: 2309
<212> TYPE: DNA
<213> ORGANISM: Homo sapiens
<220> FEATURE:
<221> NAME/KEY: CDS
<222> LOCATION: (44)...(952)

<400> SEQUENCE: 1

```
gagagactgt gccagtccca gccgccctac cgccgtggga acg atg gca gat gat        55
                                              Met Ala Asp Asp
                                                1 cag ggc tgt att gaa gag cag ggg gtt gag gat tca gca aat gaa gat      103
Gln Gly Cys Ile Glu Glu Gln Gly Val Glu Asp Ser Ala Asn Glu Asp
  5              10                  15                  20 tca gtg gat gct aag cca gac cgg tcc tcg ttt gta ccg tcc ctc ttc      151
Ser Val Asp Ala Lys Pro Asp Arg Ser Ser Phe Val Pro Ser Leu Phe
             25                  30                  35 agt aag aag aag aaa aat gtc acc atg cga tcc atc aag acc acc cgg      199
Ser Lys Lys Lys Lys Asn Val Thr Met Arg Ser Ile Lys Thr Thr Arg
         40                  45                  50 gac cga gtg cct aca tat cag tac aac atg aat ttt gaa aag ctg ggc      247
Asp Arg Val Pro Thr Tyr Gln Tyr Asn Met Asn Phe Glu Lys Leu Gly
     55                  60                  65 aaa tgc atc ata ata aac aac aag aac ttt gat aaa gtg aca ggt atg      295
Lys Cys Ile Ile Ile Asn Asn Lys Asn Phe Asp Lys Val Thr Gly Met
 70                  75                  80 ggc gtt cga aac gga aca gac aaa gat gcc gag gcg ctc ttc aag tgc      343
Gly Val Arg Asn Gly Thr Asp Lys Asp Ala Glu Ala Leu Phe Lys Cys
```

-continued

```
Gly Val Arg Asn Gly Thr Asp Lys Asp Ala Glu Ala Leu Phe Lys Cys
 85                  90                  95                 100 ttc cga agc ctg ggt ttt gac gtg att gtc tat aat gac tgc tct tgt      391
Phe Arg Ser Leu Gly Phe Asp Val Ile Val Tyr Asn Asp Cys Ser Cys
                105                 110                 115 gcc aag atg caa gat ctg ctt aaa aaa gct tct gaa gag gac cat aca      439
Ala Lys Met Gln Asp Leu Leu Lys Lys Ala Ser Glu Glu Asp His Thr
            120                 125                 130 aat gcc gcc tgc ttc gcc tgc atc ctc tta agc cat gga gaa gaa aat      487
Asn Ala Ala Cys Phe Ala Cys Ile Leu Leu Ser His Gly Glu Glu Asn
        135                 140                 145 gta att tat ggg aaa gat ggt gtc aca cca ata aag gat ttg aca gcc      535
Val Ile Tyr Gly Lys Asp Gly Val Thr Pro Ile Lys Asp Leu Thr Ala
    150                 155                 160 cac ttt agg ggg gat aga tgc aaa acc ctt tta gag aaa ccc aaa ctc      583
His Phe Arg Gly Asp Arg Cys Lys Thr Leu Leu Glu Lys Pro Lys Leu
165                 170                 175                 180 ttc ttc att cag gct tgc cga ggg acc gag ctt gat gat ggc atc cag      631
Phe Phe Ile Gln Ala Cys Arg Gly Thr Glu Leu Asp Asp Gly Ile Gln
                185                 190                 195 gcc gac tcg ggg ccc atc aat gac aca gat gct aat cct cga tac aag      679
Ala Asp Ser Gly Pro Ile Asn Asp Thr Asp Ala Asn Pro Arg Tyr Lys
            200                 205                 210 atc cca gtg gaa gct gac ttc ctc ttc gcc tat tcc acg gtt cca ggc      727
Ile Pro Val Glu Ala Asp Phe Leu Phe Ala Tyr Ser Thr Val Pro Gly
        215                 220                 225 tat tac tcg tgg agg agc cca gga aga ggc tcc tgg ttt gtg caa gcc      775
Tyr Tyr Ser Trp Arg Ser Pro Gly Arg Gly Ser Trp Phe Val Gln Ala
    230                 235                 240 ctc tgc tcc atc ctg gag gag cac gga aaa gac ctg gaa atc atg cag      823
Leu Cys Ser Ile Leu Glu Glu His Gly Lys Asp Leu Glu Ile Met Gln
245                 250                 255                 260 atc ctc acc agg gtg aat gac aga gtt gcc agg cac ttt gag tct cag      871
Ile Leu Thr Arg Val Asn Asp Arg Val Ala Arg His Phe Glu Ser Gln
                265                 270                 275 tct gat gac cca cac ttc cat gag aag aag cag atc ccc tgt gtg gtc      919
Ser Asp Asp Pro His Phe His Glu Lys Lys Gln Ile Pro Cys Val Val
            280                 285                 290 tcc atg ctc acc aag gaa ctc tac ttc agt caa tagccatatc agggtacat     972
Ser Met Leu Thr Lys Glu Leu Tyr Phe Ser Gln
        295                 300 tctagctgag aagcaatggg tcactcatta atgaatcaca ttttttatg  ctcttgaaat   1032 attcagaaat tctccaggat tttaatttca ggaaaatgta ttgattcaac agggaagaaa   1092
ctttctggtg ctgtcttttg ttctctgaat tttcagagac tttttttataa tgttattcat  1152 ttggtgactg tgtaactttc tcttaagatt aatttctct  ttgtatgtct gttaccttgt   1212
taatagactt aatacatgca acagaagtga cttctggaga aagctcatgg ctgtgtccac   1272
tgcaattggt ggtaacagtg gtagagtcat gtttgcactt ggcaaaaaga atcccaatgt   1332
ttgacaaaac acagccaagg ggatatttac tgctctttat tgcagaatgt gggtattgag   1392
tgtgatttga atgattttt c attggcttag ggcagatttt catgcaaaag ttctcatatg  1452
agttagagga gaaaaagctt aatgattctg atatgtatcc atcaggatcc agtctggaaa   1512
acagaaacca ttctaggtgt ttcaacagag ggagtttaat acaggaaatt gacttacata   1572
gatgataaaa gagaagccaa acagcaagaa gctgttacca cacccagggc tatgaggata   1632
atgggaagag gtttggtttc ctgtgtccag tagtgggatc atccagagga gctggaacca   1692
```

-continued

```
tggtgggggc tgcctagtgg gagttaggac caccaatgga ttgtggaaaa tggagccatg    1752
acaagaacaa agccactgac tgagatggag tgagctgaga cagataagag aatatccttgt   1812 ctcacctatc ctgccctcac atcttccacc agcaccttac tgcccaggcc tatctggaag   1872
ccacctcacc aaggaccttg aagagcaag ggacagtgag gcaggagaag aacaagaaat   1932
ggatgtaagc ctggcccata atgtgaacat aagtaatcac taatgctcaa caatttatcc   1992
attcaatcat ttattcattg ggttgtcaga tagtctatgt atgtgtaaaa caatctgttt   2052
tggctttatg tgcaaaatct gttatagctt taaaatatat ctggaacttt ttagattatt   2112
ccaagcctta ttttgagtaa atatttgtta cttttagttc tataagtgag aagagttta    2172 tggcaaagat ttttggcact ttgttttcaa gatggtgtta tcttttgaat tcttgataaa   2232
tgactgtttt tttctgccta atagtaactg gttaaaaaac aaatgttcat atttattgat   2292
taaaaatgtg gttgctt                                                   2309
```

<210> SEQ ID NO 2
<211> LENGTH: 303
<212> TYPE: PRT
<213> ORGANISM: Homo sapiens

<400> SEQUENCE: 2

```
Met Ala Asp Asp Gln Gly Cys Ile Glu Glu Gln Gly Val Glu Asp Ser
 1               5                  10                  15

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
    50                  55                  60

Glu Lys Leu Gly Lys Cys Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
        115                 120                 125

Glu Asp His Thr Asn Ala Ala Cys Phe Ala Cys Ile Leu Leu Ser His
    130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
    210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
```

```
                            260                       265                        270
                   Phe Glu Ser Gln Ser Asp Asp Pro His Phe His Glu Lys Lys Gln Ile
                              275                       280                       285
                   Pro Cys Val Val Ser Met Leu Thr Lys Glu Leu Tyr Phe Ser Gln
                       290                       295                       300

<210> SEQ ID NO 3
<211> LENGTH: 2377
<212> TYPE: DNA
<213> ORGANISM: Homo sapiens
<220> FEATURE:
<221> NAME/KEY: CDS
<222> LOCATION: (590)...(904)

<400> SEQUENCE: 3
gcaagctggg ctgctgggtg ggtacttcct tcaaagctga gggagcgtcc tacgcccacg        60
cgcgcaggag ggcgcccccc gcaaagcaac gtctaggaga ccacagtgga tgccacagcg       120
ggcccgaagc ggatcagcct tgtggatggc agatgatcag gctgtattg aagagcaggg        180 ggttgaggat tcagcaaatg aagattcagt ggatgctaag ccagaccggt cctcgttttgt      240 accgtccctc ttcagtaaga agaagaaaaa tgtcaccatg cgatccatca agaccacccg       300
ggaccgagtg cctacatatc agtacaacat gaattttgaa aagctgggca atgcatcat       360 aataaacaac aagaactttg ataaagtgac aggtatgggc gttcgaaacg aacagacaa       420 agatgccgag gcgctcttca gtgcttccg aagcctgggt tttgacgtga ttgtctataa        480
tgactgctct tgtgccaaga tgcaagatct gcttaaaaaa gcttctgaag aggaccatac       540
aaatgccgcc tgcttcgcct gcatcctctt aagccatgga gagaaaat atg gaa tct        598
                                                     Met Glu Ser
                                                      1 tgc tct gtc acc cag gct gga gtg cag cgg cgt gat ctc gga aga ctg         646
Cys Ser Val Thr Gln Ala Gly Val Gln Arg Arg Asp Leu Gly Arg Leu
       5                  10                  15 caa cct cca cct ccc agg ctt gcc gag gga ccg agc ttg atg atg gca         694
Gln Pro Pro Pro Pro Arg Leu Ala Glu Gly Pro Ser Leu Met Met Ala
 20                  25                  30                  35 tcc agg ccg act cgg ggc cca tca atg aca cag atg cta atc ctc gat         742
Ser Arg Pro Thr Arg Gly Pro Ser Met Thr Gln Met Leu Ile Leu Asp
                 40                  45                  50 aca aga tcc cag tgg aag ctg act tcc tct tcg cct att cca cgg ttc         790
Thr Arg Ser Gln Trp Lys Leu Thr Ser Ser Ser Pro Ile Pro Arg Phe
         55                  60                  65 cag gct att act cgt gga gga gcc cag gaa gag gct cct ggt ttg tgc         838
Gln Ala Ile Thr Arg Gly Gly Ala Gln Glu Glu Ala Pro Gly Leu Cys
     70                  75                  80 aag ccc tct gct cca tcc tgg agg agc acg gaa aag acc tgg aaa tca         886
Lys Pro Ser Ala Pro Ser Trp Arg Ser Thr Glu Lys Thr Trp Lys Ser
 85                  90                  95 tgc aga tcc tca cca ggg tgaatgacag agttgccagg cactttgagt                934
Cys Arg Ser Ser Pro Gly
100             105 ctcagtctga tgacccacac ttccatgaga agaagcagat cccctgtgtg gtctccatgc      994
tcaccaagga actctacttc agtcaatagc catatcaggg gtacattcta gctgagaagc     1054
aatgggtcac tcattaatga atcacatttt tttatgctct tgaaatattc agaaattctc     1114
caggatttta atttcaggaa aatgtattga ttcaacaggg aagaaacttt ctggtgctgt     1174
cttttgttct ctgaattttc agagactttt ttataatgtt attcatttgg tgactgtgta     1234
```

-continued

```
actttctctt aagattaatt ttctctttgt atgtctgtta ccttgttaat agacttaata      1294
catgcaacag aagtgacttc tggagaaagc tcatggctgt gtccactgca attggtggta      1354
acagtggtag agtcatgttt gcacttggca aaaagaatcc caatgtttga caaaacacag      1414
ccaaggggat atttactgct ctttattgca gaatgtgggt attgagtgtg atttgaatga      1474
tttttcattg gcttagggca gattttcatg caaaagttct catatgagtt agaggagaaa      1534
aagcttaatg attctgatat gtatccatca ggatccagtc tggaaaacag aaaccattct      1594
aggtgtttca acagagggag tttaatacag gaaattgact tacatagatg ataaaagaga      1654
agccaaacag caagaagctg ttaccacacc cagggctatg aggataatgg aagaggttt       1714 ggtttcctgt gtccagtagt gggatcatcc agaggagctg gaaccatggt gggggctgcc      1774
tagtgggagt taggaccacc aatggattgt ggaaaatgga gccatgacaa gaacaaagcc      1834
actgactgag atggagtgag ctgagacaga taagagaata ccttgtctca cctatcctgc      1894
cctcacatct tccaccagca ccttactgcc caggcctatc tggaagccac ctcaccaagg      1954
accttggaag agcaagggac agtgaggcag gagaagaaca agaaatggat gtaagcctgg      2014
cccataatgt gaacataagt aatcactaat gctcaacaat ttatccattc aatcatttat      2074
tcattgggtt gtcagatagt ctatgtatgt gtaaaacaat ctgttttggc tttatgtgca      2134
aaatctgtta tagctttaaa atatatctgg aacttttag attattccaa gccttatttt       2194
gagtaaatat ttgttacttt tagttctata agtgaggaag agtttatggc aaagattttt      2254
ggcactttgt tttcaagatg gtgttatctt ttgaattctt gataaatgac tgttttttc       2314 tgcctaatag taactggtta aaaaacaaat gttcatattt attgattaaa aatgtggttg      2374
ctt                                                                    2377
```

<210> SEQ ID NO 4
<211> LENGTH: 105
<212> TYPE: PRT
<213> ORGANISM: Homo sapiens

<400> SEQUENCE: 4

```
Met Glu Ser Cys Ser Val Thr Gln Ala Gly Val Gln Arg Arg Asp Leu
  1               5                  10                  15

Gly Arg Leu Gln Pro Pro Pro Arg Leu Ala Glu Gly Pro Ser Leu
             20                  25                  30

Met Met Ala Ser Arg Pro Thr Arg Gly Pro Ser Met Thr Gln Met Leu
         35                  40                  45

Ile Leu Asp Thr Arg Ser Gln Trp Lys Leu Thr Ser Ser Ser Pro Ile
     50                  55                  60

Pro Arg Phe Gln Ala Ile Thr Arg Gly Gly Ala Gln Glu Glu Ala Pro
 65                  70                  75                  80

Gly Leu Cys Lys Pro Ser Ala Pro Ser Trp Arg Ser Thr Glu Lys Thr
                 85                  90                  95

Trp Lys Ser Cys Arg Ser Ser Pro Gly
            100                 105
```

<210> SEQ ID NO 5
<211> LENGTH: 19
<212> TYPE: DNA
<213> ORGANISM: Artificial Sequence
<220> FEATURE:
<223> OTHER INFORMATION: Primer T50-pr1

<400> SEQUENCE: 5

```
ccgtggaata ggcgaagag                                               19

<210> SEQ ID NO 6
<211> LENGTH: 17
<212> TYPE: DNA
<213> ORGANISM: Artificial Sequence
<220> FEATURE:
<223> OTHER INFORMATION: Primer SK-Zap

<400> SEQUENCE: 6
caggaattcg gcacgag                                                 17

<210> SEQ ID NO 7
<211> LENGTH: 21
<212> TYPE: DNA
<213> ORGANISM: Artificial Sequence
<220> FEATURE:
<223> OTHER INFORMATION: Primer T50-pr3

<400> SEQUENCE: 7
gccataaact cttcctcact t                                            21

<210> SEQ ID NO 8
<211> LENGTH: 18
<212> TYPE: DNA
<213> ORGANISM: Artificial Sequence
<220> FEATURE:
<223> OTHER INFORMATION: Primer T50-pr4

<400> SEQUENCE: 8
atggcagatg atcagggc                                                18

<210> SEQ ID NO 9
<211> LENGTH: 21
<212> TYPE: DNA
<213> ORGANISM: Artificial Sequence
<220> FEATURE:
<223> OTHER INFORMATION: Primer Mch3-p20

<400> SEQUENCE: 9
ctagtcggcc tggatgccat c                                            21

<210> SEQ ID NO 10
<211> LENGTH: 21
<212> TYPE: DNA
<213> ORGANISM: Artificial Sequence
<220> FEATURE:
<223> OTHER INFORMATION: Primer  Mch3-p12

<400> SEQUENCE: 10
atgtcggggc ccatcaatga c                                            21

<210> SEQ ID NO 11
<211> LENGTH: 18
<212> TYPE: DNA
<213> ORGANISM: Artificial Sequence
<220> FEATURE:
<223> OTHER INFORMATION: Primer T50-pr9

<400> SEQUENCE: 11
gacccattgc ttctcagc                                                18

<210> SEQ ID NO 12
<211> LENGTH: 5
<212> TYPE: PRT
<213> ORGANISM: Unknown
```

```
<220> FEATURE:
<223> OTHER INFORMATION: Pentapeptide sequence that is conserved in a
      number of the ICE/Ced-3 family of proteases.

<400> SEQUENCE: 12

Gly Ser Trp Phe Ile
 1               5

<210> SEQ ID NO 13
<211> LENGTH: 5
<212> TYPE: PRT
<213> ORGANISM: Unknown
<220> FEATURE:
<223> OTHER INFORMATION: Pentapeptide sequence that is conserved in a
      number of the ICE/Ced-3 family of proteases.

<400> SEQUENCE: 13

Gly Ser Trp Tyr Ile
 1               5

<210> SEQ ID NO 14
<211> LENGTH: 5
<212> TYPE: PRT
<213> ORGANISM: Unknown
<220> FEATURE:
<223> OTHER INFORMATION: Conserved active site.

<400> SEQUENCE: 14

Gln Ala Cys Arg Gly
 1               5

<210> SEQ ID NO 15
<211> LENGTH: 4
<212> TYPE: PRT
<213> ORGANISM: Unknown
<220> FEATURE:
<223> OTHER INFORMATION: Mch3 peptidyl inhibitor

<400> SEQUENCE: 15

Asp Glu Val Asp
 1

<210> SEQ ID NO 16
<211> LENGTH: 4
<212> TYPE: PRT
<213> ORGANISM: Unknown
<220> FEATURE:
<223> OTHER INFORMATION: Mch3 peptidyl inhibitor

<400> SEQUENCE: 16

Tyr Val Ala Asp
 1

<210> SEQ ID NO 17
<211> LENGTH: 4
<212> TYPE: PRT
<213> ORGANISM: Unknown
<220> FEATURE:
<223> OTHER INFORMATION: Mch3 peptidyl inhibitor

<400> SEQUENCE: 17

Asp Ser Val Asp
 1
```

MCH3, A NOVEL APOPTOTIC PROTEASE, NUCLEIC ACIDS ENCODING AND METHODS OF USE

This patent is a divisional of U.S. patent application Ser. No. 09/944,851 (filed Aug. 31, 2001) now abandoned, which, in turn, is a continuation of U.S. patent application Ser. No. 08/556,627 (filed Nov. 13, 1995) now U.S. Pat. No. 6,462,175.

This invention was made with government support under grants AI 35035-01 from the National Institutes of Health. Accordingly, the government has certain rights to this invention.

Throughout this application various publications are referenced within parentheses. The disclosures of these publications in their entireties are hereby incorporated by reference in this application in order to more fully describe the state of the art to which this invention pertains.

BACKGROUND OF THE INVENTION

The present invention relates generally to apoptosis or, programed cell death, and more particularly, to a novel cysteine protease which can be used to modulate apoptosis for the therapeutic treatment of human diseases.

Apoptosis is a normal physiological process of cell death that plays a critical role in the regulation of tissue homeostasis by ensuring that the rate of new cell accumulation produced by cell division is offset by a commensurate rate of cell loss due to death. It has now become clear that disturbances in apoptosis (also referred to as physiological cell death or programmed cell death) that prevent or delay normal cell turnover can be just as important to the pathogenesis of diseases as are known abnormalities in the regulation of proliferation and the cell cycle. Like cell division, which is controlled through complex interactions between cell cycle regulatory proteins, apoptosis is similarly regulated under normal circumstances by the interaction of gene products that either induce or inhibit cell death.

The stimuli which regulate the function of these apoptotic gene products include both extracellular and intracellular signals. Either the presence or the removal of a particular stimuli can be sufficient to evoke a positive or negative apoptotic signal. For example, physiological stimuli that prevent or inhibit apoptosis include, for example, growth factors, extracellular matrix, CD40 ligand, viral gene products neutral amino acids, zinc, estrogen and androgens. In contrast, stimuli which promote apoptosis include growth factors such as tumor necrosis factor (TNF), Fas, and transforming growth factor β (TGFβ), neurotransmitters, growth factor withdrawal, loss of extracellular matrix attachment, intracellular calcium and glucocorticoids, for example. Other stimuli, including those of environmental and pathogenetic origins, also exist which can either induce or inhibit programmed cell death. Although apoptosis is mediated by diverse signals and complex interactions of cellular gene products, the results of these interactions ultimately feed into a cell death pathway that is evolutionarily conserved between humans and invertebrates.

Several gene products which modulate the apoptotic process have now been identified. Although these products can in general be separated into two basic categories, gene products from each category can function to inhibit or induce programmed cell death. One family of gene products are those which are members of the Bcl-2 family of proteins. Bcl-2, is the best characterized member of this family and inhibits apoptosis when overexpressed in cells. Other members of this gene family include, for example, Bax, Bak, Bcl-$x_L$, Bcl-$x_S$, and Bad. While some of these proteins can prevent apoptosis others augment apoptosis (e.g. Bcl-$x_L$ and Bak, respectively).

A second family of gene products, the interleukin-1-beta converting enzyme (ICE) family of proteases are related genetically to the C. elegans Ced-3 gene product which was initially shown to be required for programmed cell death in the roundworm, C. elegans. The ICE family of proteases includes human ICE, ICH-$1_L$, ICH-$1_S$, CPP32, Mch2, ICH-2 and $ICE_{rel}$-III. Among the common features of these gene products is that 1) they are cysteine proteases with specificity for substrate cleavage at Asp-x bonds, 2) they share a conserved pentapeptide sequence (QACRG) (SEQ ID NO: 14) within the active site and 3) they are synthesized as proenzymes that require proteolytic cleavage at specific aspartate residues for activation of protease activity. Cleavage of the proenzyme produces two polypeptide protease subunits of approximately 20 kD (p20) and 10 kD (p10) which, in the case of ICE, combine non-covalently to form a tetramer comprised of two p20:p10 heterodimers. Although these proteases, when expressed in cells, induce cell death, several alternative structural forms of these proteases, such as ICEδ, ICEε, ICH-$1_s$ and Mch2β, actually function to inhibit apoptosis.

In addition to the Bcl-2 and Ced-3/ICE gene families which play a role in apoptosis in mammalian cells, it has become increasingly apparent that other gene products exist which are important in mammalian cell death and which have yet to be identified. For example, in addition to Ced-3, another C. elegans gene known as Ced-4 exists which is also required for programmed cell death in C. elegans. However, mammalian homologues of this protein remain elusive and have not yet been identified. Further, it is ambiguous as to whether other genes exist which belong to either of the above two apoptotic gene families or what role they may play in the programmed cell death pathway.

As stated previously, apoptosis plays an important physiological role in maintaining tissue homeostasis. Programmed cell death functions in physiological processes such as embryonic development, immune cell regulation and normal cellular turnover. Therefore, the dysfunction, or loss of regulated apoptosis can lead to a variety of pathological disease states. For example, the loss of apoptosis can lead to the pathological accumulation of self-reactive lymphocytes such as that occurring with many autoimmune diseases. Inappropriate loss of apoptosis can also lead to the accumulation of virally infected cells and of hyperproliferative cells such as neoplastic or tumor cells Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can change the natural progression of many of these diseases.

Thus, there exists a need to identify new apoptotic genes and their gene products and for methods of modulating this process for the therapeutic treatment of human diseases. The present invention satisfies this need and provides related advantages as well.

SUMMARY OF THE INVENTION

The invention provides an isolated gene encoding Mch3, or functional fragment thereof. Also provided is an isolated nucleic acid sequence encoding Mch3 or functional fragment thereof. The gene or nucleic acid sequence can be single or double stranded nucleic acids corresponding to coding or non-coding strands of the Mch3 nucleotide sequence. An isolated Mch3 polypeptide or functional fragment thereof is also provided.

BRIEF DESCRIPTION OF THE DRAWINGS

FIG. 1 shows the nucleotide and predicted amino acid sequence of the human Mch3α of (SEQ ID NOS:1 and 2) and Mch3β (SEQ ID NOS:3 and 4), respectively. The nucleotide sequence of Mch3β that is different from that of Mch3α is shown below the nucleotide sequence of Mch3α. The predicted amino acid sequence of Mch3α is shown above the nucleotide sequence. The predicted amino acid sequence of Mch3β that is different from that of Mch3α is shown below the nucleotide sequence. Dotted lines indicate the spliced sequences in Mch3α and β. The underlined Mch3α nucleotide sequence is deleted in Mch3β and is replaced by the intronic sequence shown below it. The putative active site pentapeptide of Mch3α is boxed. The putative p20, p17 and p12 cleavage sites are indicated with a horizontal arrow. The vertical arrow indicates an intron location. Amino acid and nucleotide residues are numbered to the right of each sequence.

Figure 2:
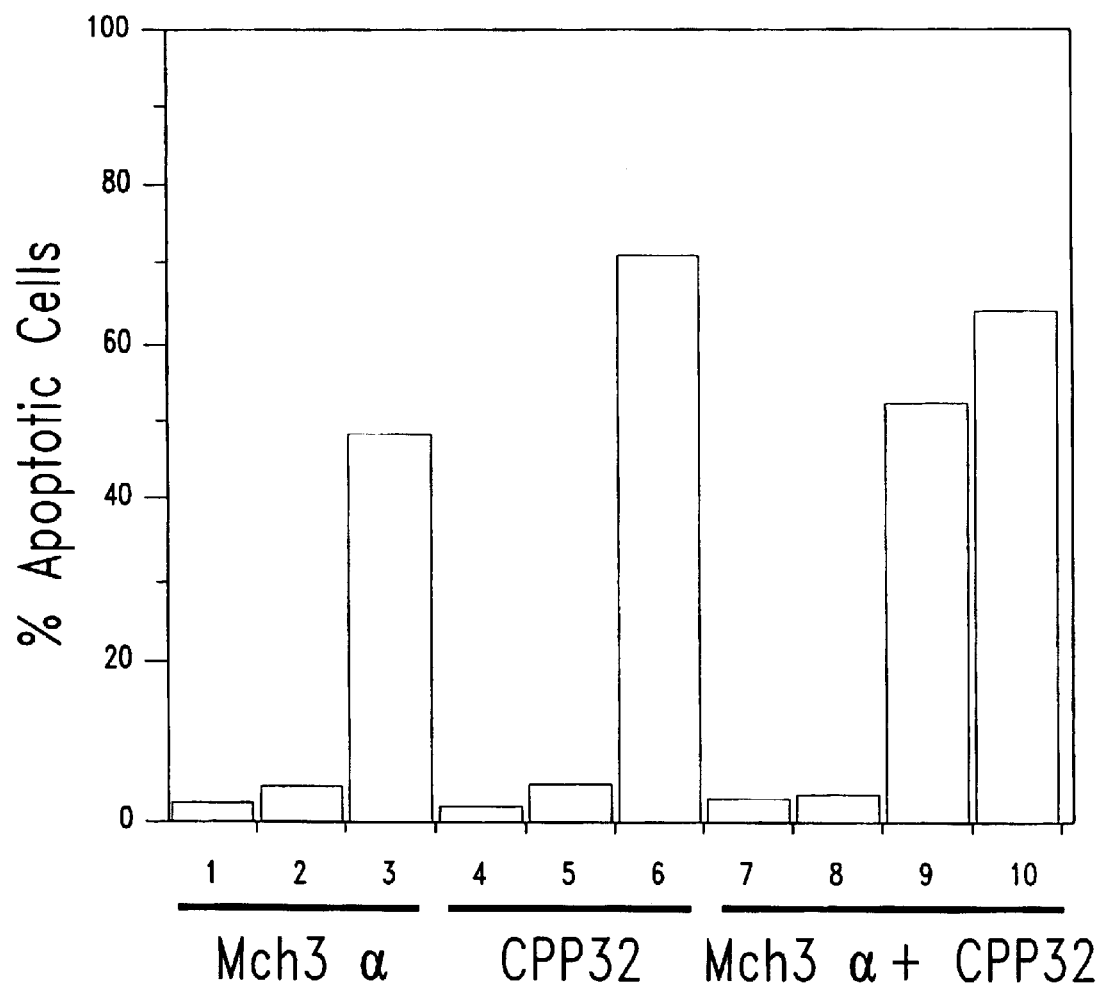
FIG. 2 shows Sf9 cells that were infected with the following recombinant baculoviruses: column 1, AcNPV-Mch3α-p17; column 2, AcNPV-Mch3α-p12; column 3, AcNPV-Mch3α-p17 and AcNPV-Mch3α-p12; column 4, AcNPV-CPP32-p17; column 5, AcNPV-CPP32-p12; column 6, AcNPV-CPP32-p17 and AcNPV-CPP32-p12; column 7, AcNPV-MCH3α-p17 and AcNPV-CPP32-p17; column 8, AcNPV-Mch3α-p12 and AcNPV-CPP32-p12; column 9, AcNPV-Mch3α-p17 and AcNPV-CPP32-p12; column 10, AcNPV-CPP32-p17 and AcNPV-Mch3α-p12. 42 h postinfection, cells were examined microscopically and several fields were counted (average 1500 cells/condition) and the number of apoptotic cells was expressed as a percentage of total cells counted.

(A) pbluescript vectors containing a GST-Mch3α2 or a GST-CPP32 inserts under the T7 promoter were linearized with the appropriate restriction enzymes as indicated by arrows and then used as templates for in vitro transcription and translation in the presence of $^{35}$S-methionine.

(B) Lanes 1 and 2, the GST-Mch3α2 DNA template was linearized with Eco RI before transcription/translation and the products of translation were incubated with buffer (lane 1) or CPP32 (lane 2) for 30 min at 30° C. Small amount of full length GST-Mch3α2 can be seen as a 64 kDa translation product (lane 1) or 35 kDa cleavage product due to incomplete digestion of the DNA template with Eco RI. Lanes 3–6, The GST-Mch3α2 DNA template was linearized with Xho I before transcription/translation and the products of translation were incubated for 30 min on ice with buffer (lane 3) or at 30° C. with buffer (lane 4), CPP32 (lane 5) or Mch3α (lane 6).

(C) The GST-CPP32 DNA template was linearized with Eco RI before transcription/translation and the products of translation were incubated for 30 min at 30° C. with buffer (lane 1), Mch3α (lane 2) or CPP32 (lane 3).

(D) The GST-Mch3α was immobilized on a GST-Sepharose resin and the resin-GST-Mch3α2 was incubated for 1 h on ice with buffer (lane 1) or with CPP32 (lane 2) at 30° C. The protein products in B and C were analyzed on a 14% SDS-gels and in D on a 10–20% gradient SDS-gels. The arrows on the right of B and C indicate the cleavage products.

DETAILED DESCRIPTION OF THE INVENTION

This invention is directed to a novel apoptotic cysteine protease termed Mch3. This protease is a member of the ICE family of cysteine protease which includes, for example, ICE, ICH-1$_L$, ICH-1$_S$, CPP32, Mch2, ICH-2 and ICE$_{rel}$-III. Similar to other ICE related proteases, Mch3 is synthesized as a larger proenzyme and becomes active following proteolytic cleavage into two subunits of approximately 17 kD (p17) and 12 kD (p12). The two subunits form heterodimers which associate with each other into an active complex. Mch3 contains no known functionally significant sequence identities outside of the ICE family of cysteine proteases. Similar to these other cysteine proteases, substrate specificity uniquely requires an Asp residue in the P1 position of the substrate binding site with a small, preferably hydrophobic, residue in the P1' position. Overexpression of Mch3 protease results in the induction of apoptosis.

In one embodiment, the invention is directed to nucleic acids encoding the apoptotic cysteine protease Mch3. The nucleic acids are used to produce recombinant Mch3 protease, whose activity can be measured enzymatically. The recombinant Mch3 polypeptides are used to screen for Mch3 inhibitory compounds. Such pharmaceutical compounds are useful for the treatment or prevention of diseases which are characterized by apoptotic cell death Alternatively, the Mch3 polypeptides can be used to screen for pharmaceutical compounds which activate or act as agonists of Mch3 such as by inducing cleavage of the proenzyme into its active subunits. Such compounds are useful for the treatment or prevention of diseases which are characterized by the loss of apoptotic cell death.

Figure 1A:
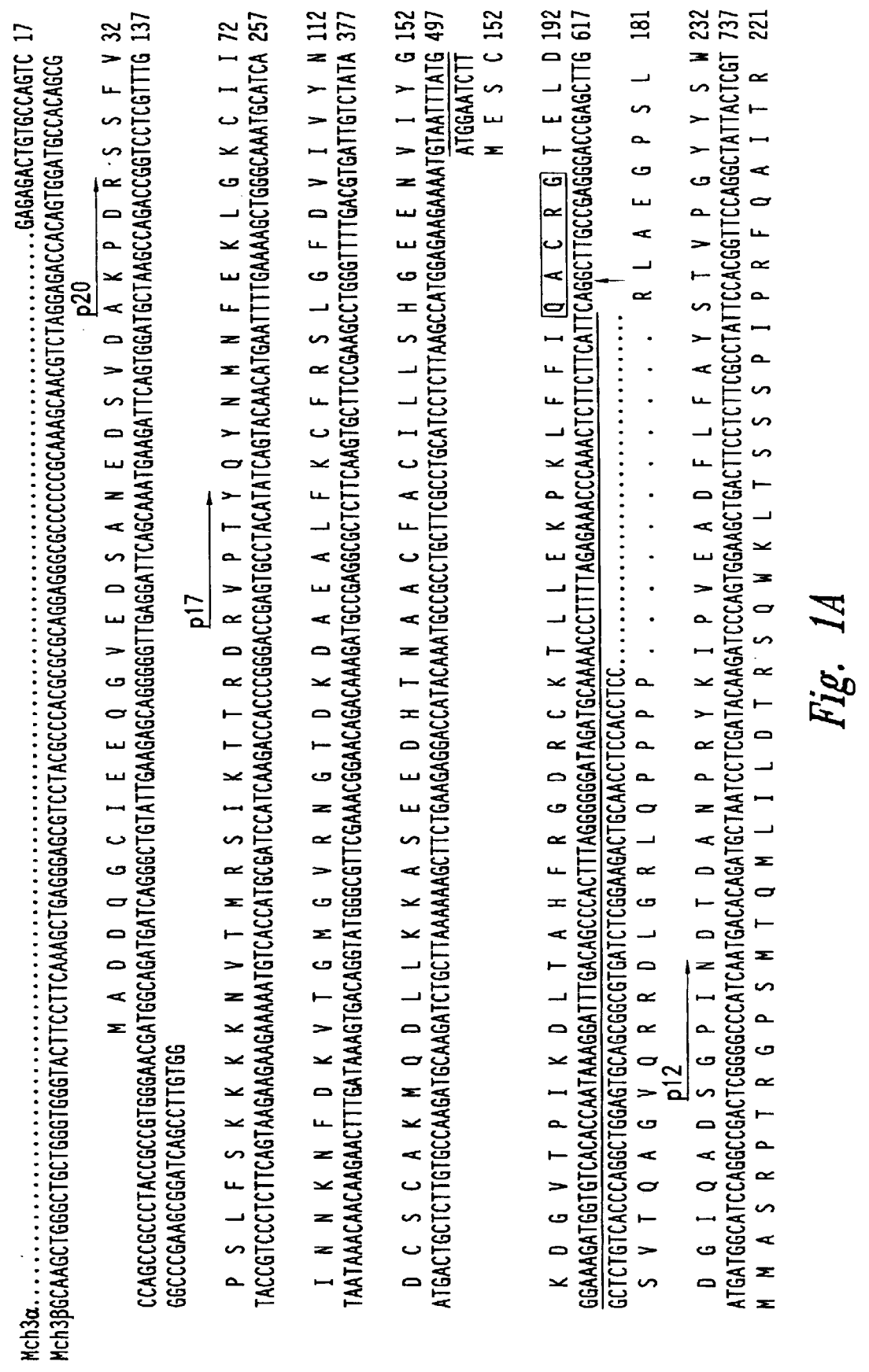

As used herein, the term "substantially" when referring to a Mch3 nucleotide or amino acid sequence is intended to refer to the degree to which two sequences of between about 15–30 or more nucelotides in length, are identical or similar so as to be considered by those skilled in the art to be functionally equivalent. For example, the Mch3 nucleic acids of the invention have a nucleotide sequence substantially the same as that shown in FIG. 1 and in SEQ ID NOS: 1 and 3. Thus, if a second sequence is substantially the same as that shown in FIG. 1 (SEQ ID NOS: 1 and 3), then it is considered functionally equivalent by those skilled in the art. Methods for sequence comparisons and determinations of similarity are well known and routine within the art.

Functionally equivalent nucleic acid sequences include, for example, sequences that are related, but different and encode the same Mch3 polypeptide due to the degeneracy of the genetic code as well as sequences that are related, but different and encode a different Mch3 polypeptide that exhibits similar functional activity. In both cases, the nucleic acids encode functionally equivalent gene products. Functional fragments of Mch3 encoding nucleic acids such as oligonucleotides, polyoligonucleotides, primers and the like are also considered to be within the definition of the term and the invention as claimed. Functional equivalency is also relevant to Mch3 nucleic acids which do not encode gene products, for example, but instead are functional elements in and of themselves. Specific examples of such functional nucleic acids include, for example, promoters, enhancers and other gene expression regulatory elements.

Mch3 polypeptides of the invention have an amino acid sequence substantially similar to that shown in FIG. 1 and in SEQ ID NOS:2 and 4. Functionally equivalent Mch3 amino acid sequences similarly includes, for example, related, but different sequences so long as the different polypeptide exhibits at least one functional activity of Mch3. Such related, but different polypeptides include, for example, substitutions of conserved and non-essential amino acids. Fragments and functional domains of Mch3 are similarly included within the definition of the term and the claimed invention.

Therefore, it is understood that limited modifications may be made without destroying the biological function of the Mch3 polypeptide and that only a portion of the entire primary structure may be required in order to effect activity. For example, minor modifications of the Mch3 amino acid sequences (SEQ ID NOS: 2 and 4) which do not destroy their activity also fall within the definition of Mch3 and within the definition of the polypeptide claimed as such. Also, for example, genetically engineered fragments of Mch3 either alone or fused to heterologous proteins such as fusion proteins, for example, that retain measurable enzymatic activity fall within the definition of the polypeptides claimed as such. It is understood that minor modifications of primary amino acid sequence may result in polypeptides which have substantially equivalent or enhanced function as compared to the sequence set forth in FIG. 1 (SEQ ID NOS 2 and 4). These modifications may be deliberate, as through site-directed mutagenesis, or may be accidental such as through mutation in hosts which are Mch3 producers. All of these modifications are included as long as Mch3 biological function is retained. Further, various molecules can be attached to Mch3, for example, other proteins, carbohydrates, lipids, or chemical moieties. Such modifications are included within the definition of Mch3 polypeptides.

The invention provides a gene encoding Mch3, or fragment thereof. The invention also provides an isolated nucleic acid sequence encoding Mch3, or fragment thereof. The gene and nucleic acid sequences encode substantially the sequence as shown in SEQ ID NOS:1 and 3. Fragments of the gene or nucleic acid sequence are provided which comprise single or double stranded nucleic acids having substantially the sequences shown in SEQ ID NOS:1 and 3.

The Mch3 nucleic acids of the present invention were identified and isolated by a novel approach of searching a human database of expressed sequence tags (ESTs) under various stringencies to identify potential new sequence fragments which may have homology to the ICE family of cysteine proteases. Novel sequences identified as having potential homology to the ICE family of apoptotic proteases can be used to design primers for attempting PCR amplification. The second primer is designed to encompass homologous regions in nucleic acid sequences that encode known ICE protease family members. In this specific case, the primer was directed to the GSWFI/GSWYI (SEQ ID NOS: 12–13) pentapeptide sequence that is conserved in a number of the ICE/Ced-3 family of proteases. The primer design should take into account the predicted strandedness of both the EST sequence primer and the known primer. Thus, only if the homology search and hybridization conditions are successfully determined, will such an approach allow PCR amplification of a fragment of the putative novel protease cDNA. As searching a genetic data base will yield homologous sequence matches to any query nucleotide sequence, additional criteria must be used to identify the authentic ICE family homologue from among the non-specific homology matches. ICE family members share the highest degree of homology in the active site and catalytically important amino acid residues. A given EST returned by the search may not include one of these highly homologous sites, but rather, may only include a region within the protease with cryptic homology. Confirming an EST as a novel ICE protease involves translation of all the positive EST hits in three different reading frames and subsequent identification of conservative active site or catalytically important amino acid sequence motifs. Then, using conventional cDNA cloning, a full length cDNA of the putative novel protease can be obtained and 1) analyzed for overall structural homology to ICE family members, 2) recombinantly expressed and analyzed for cysteine protease activity, and 3) analyzed for the induction of programmed cell death by heterologous expression of the cDNA in appropriate cells.

Alternative methods than that described above for isolating Mch3 encoding nucleic acids can similarly be employed. For example, using the teachings described herein, those skilled in the art can routinely isolate and manipulate Mch3 nucleic acids using methods well known in the art. All that is necessary is the sequence of the Mch3 encoding nucleic acids (FIG. 1 and SEQ ID NOS:1 and 3) or the Mch3 amino acid sequence (FIG. 1 and SEQ ID NOS:2 and 4). Such methods include, for example, screening a cDNA or genomic library by using synthetic oligonucleotides, nucleic acid fragments or primers as hybridization probes. Alternatively, antibodies to the Mch3 amino acid sequence or fragments thereof can be generated and used to screen an expression library to isolate Mch3 encoding nucleic acids. Other binding reagents to Mch3 polypeptides can similarly be used to isolate Mch3 polypeptides having substantially the amino acid sequence show in FIG. 1. Similarly, substrate reagents such as non-cleavable peptide analogues of cysteine proteases can be used to screen and isolate Mch3 polypeptides.

In addition, recombinant DNA methods currently used by those skilled in the art include the polymerase chain reaction (PCR) which, combined with the Mch3 nucleotide and amino acid sequences described herein, allows easy reproduction of Mch3 encoding sequences. Desired sequences can be amplified exponentially starting from as little as a single gene copy by means of PCR. The PCR technology is the subject matter of U.S. Pat. Nos. 4,683,195, 4,800,159, 4,754,065, and 4,683,202 all of which are incorporated by reference herein.

The above described methods are known to those skilled in the art and are described, for example, in Sambrook et al., *Molecular Cloning: A Laboratory Manual*, Cold Spring Harbor Laboratory, New York (1992) and the various references cited therein and in Ansubel et al., *Current Protocols in Molecular Biology*, John Wiley and Sons, Baltimore, Md. (1989); and in Harlow et al., *Antibodies: A Laboratory Manual*, Cold Spring Harbor Laboratory, New York (1989). These references and the publications cited therein are hereby expressly incorporated herein by reference.

The invention provides an isolated Mch3 polypeptide comprising substantially the amino acid sequence as that shown in FIG. 1 (SEQ ID NOS:2 and 4). Mch3 functional fragments are also provided. A specific example of an Mch3 functional fragment is the catalytic domain which contains the active site amino acid sequence QACRG.

Isolated Mch3 polypeptides of the invention can be obtained by a variety of methods known within the art. For example, the isolated peptides can be purified by biochemical methods including, for example, affinity chromatography. Affinity matrices which can be used for Mch3 isolation can be anti-Mch3 monoclonal or polyclonal antibodies prepared against the sequence shown in FIG. 1 (SEQ ID NOS:2 and 4), or fragments thereof such as synthetic peptides.

Alternatively, substrate analogues or enzymatic inhibitors of Mch3 can similarly be used as affinity matrices to isolate substantially pure Mch3 polypeptides of the invention.

Mch3 polypeptides can also be produced by recombinant methods known to those skilled in the art. Recombinant Mch3 polypeptides include, for example, an amino acid sequence substantially the same as that shown in FIG. 1 (SEQ ID NOS:2 and 4) as well as fusion proteins and fragments thereof. The Mch3 encoding nucleic acids can be cloned into the appropriate vectors for propagation, manipulation and expression. Such vectors are known or can be constructed by those skilled in the art and should contain all expression elements necessary for the transcription, translation, regulation, and if desired, sorting of the Mch3 polypeptides. The vectors can also be for use in either procaryotic or eucaryotic host systems so long as the expression and regulatory elements are of compatible origin. One of ordinary skill in the art will know which host systems are compatible with a particular vector. The recombinant polypeptides produced can be isolated by the methods described above.

Apoptosis plays a significant role in numerous pathological conditions in that programed cell death is either inhibited, resulting in increased cell survival, or enhanced which results in the loss of cell viability. Examples of pathological conditions resulting from increased cell survival include cancers such as lymphomas, carcinomas and hormone dependent tumors. Such hormone dependent tumors include, for example, breast, prostrate and ovarian cancer. Autoimmune diseases such as systemic lupus erythematosus and immune-mediated glomerulonephritis as well as viral infections such as herpesvirus, poxvirus and adenovirus also result from increased cell survival or the inhibition of apoptosis.

In contrast, apoptotic diseases where enhanced programed cell death is a prevalent cause generally includes, for example, degenerative disorders such as Alzheimer's disease, Parkinson's disease, Amyotrophic lateral sclerosis, Retinitis pigmentosa, and Cerebellar degeneration. Other diseases associated with increased apoptosis include, for example, myelodysplastic syndromes such as aplastic anemia and ischemic injury including myocardial infarction, stroke and reperfusion injury.

The Mch3 encoding nucleic acids and polypeptides of the invention can be used to diagnose, treat or reduce the severity of cell death mediated diseases such as those described above as well as other diseases mediated by either increased or decreased programmed cell death. Additionally, the Mch3 encoding nucleic acids and polypeptides of the invention can be used to screen for pharmaceutical compounds and macromolecules which inhibit or promote Mch3 mediated apoptosis.

For example, the Mch3 encoding nucleic acids, polypeptides and functional fragments thereof can be used to diagnose, or to generate reagents to diagnose diseases mediated or characterized by programed cell death. Diagnosis can be by nucleic acid probe hybridization with Mch3 containing nucleotide sequences, antibody or ligand mediated detection with Mch3 binding agents or by enzyme catalysis of detectable Mch3 substrates. Such methods are routine to those skilled in the art. Detection can be performed ex vivo, for example, by removing a cell or tissue sample from an individual exhibiting or suspected of exhibiting a cell death mediated disease. Correlation of increased Mch3 expression or activity is indicative of diseases characterized by enhanced programmed cell death whereas correlation of decreased Mch3 expression or activity is indicative of diseases characterized by the inhibition of programmed cell death.

The above Mch3 polypeptides can also be formulated into pharmaceutical compositions known within the art for the treatment of cell death mediated diseases characterized by increased cell survival and proliferation. Functional fragments and peptides such as the catalytic domain of Mch3 can similarly be formulated for the treatment of such diseases associated with increased cell survival and proliferation. Administration of Mch3 polypeptides and functional fragments thereof will induce apoptosis in treated cells and eliminate those cells characterized by increased cell survival or proliferation. Administration of non-Mch3 polypeptides that do not directly act on Mch3 substrates but induce the activation of the Mch3 protease can similarly be used for the treatment of diseases characterized by increased cell survival and proliferation.

To be effective, the Mch3 polypeptides must be introduced into the cells characterized by increased cell survival. Introduction can be accomplished by a variety of means known within the art including, for example, lipid vesicles and receptor mediated endocytosis. Targeting to the appropriate cell type can similarly be accomplished through conjugation to specific receptor ligands, specific target cell antibodies and the like.

The Mch3 polypeptides are administered by conventional methods, in dosages which are sufficient to induce apoptosis in the cells characterized by increased cell survival or proliferation. Such dosages are known or can be easily determined by those skilled in the art. Administration can be accomplished by, for example, intravenous, interperitonal or subcutaneous injection. Administration can be performed in a variety of different regimes which include single high dose administration or repeated small dose administration or a combination of both. The dosing will depend on the cell type, progression of the disease and overall health of the individual and will be known or can be determined by those skilled in the art.

In contrast to the induction of Mch3 mediated apoptosis for the treatment of pathological conditions characterized by increased cell survival or proliferation, inhibitors of Mch3 can be used to treat diseases characterized by increased programmed cell death. Such inhibitors can be, for example, anti-Mch3 antibodies, proteins, or small peptidyl protease inhibitors which are formulated in a medium which allows introduction into the desired cell type. Alternatively, such inhibitors can be attached to targeting ligands for introduction by cell mediated endocytosis and other receptor mediated events. Specific examples of Mch3 peptidyl inhibitors are described in Table I of Example II and includes suicide inhibitors and substrate analogues such as the tetrapeptide DEVD aldehyde (SEQ ID NO: 15), YVAD aldehyde (SEQ ID NO: 16) and the cowpox virus protein Crm A, for example. Other inhibitors of Mch3 include, for example, small molecules and organic compounds which bind and inactivate Mch3 by a competitive or non-competitive type mechanism. Molecules or compounds which indirectly inhibit the Mch3 pathway can also be used as inhibitors of Mch3. Mch3 inhibitors can be identified by screening for molecules which demonstrate specific or beneficial Mch3 inhibitory activity. Such methods are described further below and can be practiced by those skilled in the art given the Mch3 nucleotide and amino acid sequences described herein.

Dominant/negative inhibitors of Mch3 can also be used to treat or reduce the severity of diseases characterized by increased programmed cell death. In this regard, Mch3β polypeptides which lack the active site QACRG (SEQ ID NO: 14) can be used to bind p12 subunits of Mch3 and prevent active tetrameric complexes from forming. The mechanism of Mch3β dominant inhibition of Mch3α is indicated to be similar to the dominant negative inhibition of Ich-1$_L$ by Ich-1$_s$. Subunits from other ICE related cysteine proteases can similarly be used as dominant/negative inhibitors of Mch3 activity and therefore treat diseases mediated by programmed cell death. Such subunits should be selected so that they bind either the p17 or p12 Mch3 polypeptides and prevent their assembly into active tetrameric protease complexes. Moreover, Mch3 subunits which have been modified so as to be catalytically inactive can also be used as dominant negative inhibitors of Mch3. Such modifications include, for example, mutation of the active site cysteine residue to include but not limited to Alanine or glycine.

Mch3 substrate antagonists can similarly be used to treat or reduce the severity of diseases mediated by increased programmed cell death. Such substrate antagonists can bind to and inhibit cleavage by Mch3. Inhibition of substrate cleavage prevents commitment progression of programmed cell death. Substrate antagonists include, for example, ligands and small molecule compounds.

Treatment or reduction of the severity of cell death mediated diseases can also be accomplished by introducing expressible nucleic acids encoding Mch3 polypeptides or functional fragments thereof into cells characterized by such diseases. For example, elevated synthesis rates of Mch3 can be achieved by, for example, using recombinant expression vectors and gene transfer technology. Such methods are well known within the art and will be described below with reference to recombinant viral vectors. Other vectors compatible with the appropriate targeted cell can accomplish the same goal and therefore can be substituted in the methods described herein in place of recombinant viral vectors.

Recombinant viral vectors are useful for in vivo expression of a desired nucleic acid because they offer advantages such as lateral infection and targeting specificity. Lateral infection is inherent in the lifecycle of, for example, retroviruses and is the process by which a single infected cell produces many progeny virions that bud off and infect neighboring cells. The result is a large area becomes rapidly infected, most of which were not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Typically, viruses infect and propagate in specific cell types. Therefore, the targeting specificity of viral vectors utilizes this natural specificity to in turn specifically introduce a desired gene into predetermined cell types. The vector to be used in the methods of the invention will depend on desired cell type to be targeted. For example, if neurodegenerative diseases are to be treated by decreasing the Mch3 activity of affected neuronal cells then a vector specific for cells of the neuronal cell lineage should be used. Likewise, if diseases or pathological conditions of the hematopoietic system are to be treated, than a viral vector that is specific for blood cells and their precursors, preferably for the specific type of hematopoietic cell, should be used. Moreover, such vectors can additionally be modified with specific receptors or ligands and the like to modify or alter target specificity through receptor mediated events. These modification procedures can be performed by, for example, recombinant DNA techniques or synthetic chemistry procedures. The specific type of vector will depend upon the intended application. The actual vectors are also known and readily available within the art or can be constructed by one skilled in the art using well known methodology.

Viral vectors encoding Mch3 nucleic acids or inhibitors of Mch3 can be administered in several ways to obtain expression of such sequences and therefore either increase or decrease the activity of Mch3 in the cells affected by the disease or pathological condition. If viral vectors are used, for example, the procedure can take advantage of their target specificity and consequently, do not have to be administered locally at the diseased site. However, local administration can provide a quicker and more effective treatment. Administration can also be performed by, for example, intravenous or subcutaneous injection into the subject. Injection of the viral vectors into the spinal fluid can also be used as a mode of administration, especially in the case of neurodegenerative diseases. Following injection, the viral vectors will circulate until they recognize host cells with the appropriate target specificity for infection.

As described above, one mode of administration of Mch3 encoding vectors can be by direct inoculation locally at the site of the disease or pathological condition. Local administration is advantageous because there is no dilution effect and therefore a smaller dose is required to achieve Mch3 expression in a majority of the targeted cells. Additionally, local inoculation can alleviate the targeting requirement required with other forms of administration since a vector can be used that infects all cells in the inoculated area. If expression is desired in only a specific subset of cells within the inoculated area then promoter and expression elements that are specific for the desired subset can be used to accomplish this goal. Such non-targeting vectors can be, for example, viral vectors, viral genomes, plasmids, phagemids and the like. Transfection vehicles such as liposomes can be used to introduce the non-viral vectors described above into recipient cells within the inoculated area Such transfection vehicles are known by one skilled within the art. Alternatively, however, non-targeting vectors can be administered directly into a tissue of any individual. Such methods are known within the art and are described by, for example, Wolff et al. (*Science* 247:1465–1468 (1990)).

Additional features can be added to the vectors to ensure safety and/or enhance therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce mutant forms of Mch3, dysfunction of apoptosis will not occur.

As described previously, the Mch3 encoding nucleic acids and Mch3 polypeptides of the invention can be used to screen for compounds which inhibit or enhance the expression of Mch3 protease activity. Such screening methods are known to those skilled in the art and can be performed by either in vitro or in vivo procedures. For example, described in Example II is a specific in vitro assay for Mch3 activity. This assay employs Mch3 polypeptide expressed in an active, processed form recombinantly in *E. coli*, whose protease activity is measured by incubation with a fluorescent substrate (DEVD-AMC). Also described therein are peptide and polypeptide inhibitors of Mch3. This assay can be used to screen synthetic or naturally occurring compound libraries, including macromolecules, for agents which either inhibit or enhance Mch3 activity. The Mch3 polypeptides to be used in the assay can be obtained by, for example, in vitro translation, recombinant expression or biochemical procedures. Methods other than that described in Example II can also be used to screen and identify compounds which inhibit Mch3. A specific example is phage display peptide libraries where greater than $10^8$ peptide sequences can be screened in a single round of panning. Such methods as well as others are known within the art and can be utilized to identify compounds which inhibit or enhance Mch3 activity.

It is understood that modifications which do not substantially affect the activity of the various embodiments of this invention are also included within the definition of the invention provided herein. Accordingly, the following examples are intended to illustrate but not limit the present invention.

EXAMPLE I

Cloning and Characterization of Mch3

This Example shows the cloning, sequence analysis and tissue distribution of Mch3. The results described herein indicate that Mch3 is a novel member of the ICE family of cysteine proteases.

To identify potentially novel members of the ICE family of cysteine proteases, an approach combining information from the GenBank database of human expressed sequence tags (ESTs) and PCR was employed. Initially, Ced-3/ICE-like apoptotic cysteine proteases from Jurkat T-lymphocytes were enriched by amplification of a human Jurkat cDNA library using degenerate PCR primers encoding the conserved GSWFI/GSWYI (SEQ ID NO: 12–13) pentapeptides (Fernandes-Alnemri et al., *Cancer Res.* 55:2737–2742 (1995)). This amino acid sequence has been found to be conserved among ICE family members. Briefly, a 10 μl aliquot of human Jurkat λ Uni-Zap™ XR cDNA library containing approximately $10^8$ pfu was denatured at 99° C. for 5 min. and used as a substrate for PCR amplification with a degenerate primer encoding the pentapeptide GSWFI/GSWYI (SEQ ID NO: 12–13) and a T3 vector-specific primer (Stratagene).

The enriched library was then amplified with a primer derived from an EST sequence (T50828) identified in a homology search of the GenBank database using a query nucleotide sequence corresponding to the CPP32 cDNA sequence minus the untranslated nucleotides (e.g. CPP32 coding sequence). This secondary amplification was performed starting with a 10 μl aliquot of the above amplified sequences combined with a primer derived from the GenBank sequence T50828 (primer T50-pr1: CCGTGGAATAGGCGAAGAG, SEQ ID NO: 5) and a second vector specific primer (SK-Zap: CAGGAATTCGGCACGAG, SEQ ID NO: 6). The secondary amplification products were cloned into a Sma I cut pBluescript II KS$^+$ vector. All clones were screened by PCR using a degenerate oligonucleotide corresponding to the conserved active site amino acid sequence QACRG and the SK-Zap primer. Clones that were positive for the presence of the QACRG coding sequence were then subjected to DNA sequencing using T3 and T7 sequencing primers (Stratagene). This amplification and screen resulted in the identification of a Ced-3/ICE-like partial cDNA with high homology to CPP32 and Ced-3. The partial cDNA was then excised from the vector, radiolabeled and used to screen the original Jurkat λ Uni-Zap™ XR cDNA library. Positive λ clones were purified, rescued into the pBluescript II SK$^-$ plasmid vector and sequenced.

The second screen of the Jurkat X Uni-Zap™ XR cDNA library resulted in the isolation of several cDNA clones. One cDNA, named Mch3, contains an open reading frame of 909 bp that encodes a 303 amino acid protein with a predicted molecular mass of approximately 34 kD (FIG. 1 and SEQ ID NOS: 1 and 2). The initiator methionine at nucleotide 44 conforms to the consensus Kozak translation initiation sequence (20). A second cDNA clone named Mch3β (SEQ ID NO: 3) was also identified and found to contain a deletion and insertion corresponding to nucleotides 488–592 (amino acids 149–183) of the Mch3α sequence (FIG. 1) (SEQ ID NO: 1). Mch3α also has a longer 5' nontranslated sequence.

Exon/Intron analysis of the Mch3 genomic region that correspond to the deletion/insertion in Mch3β revealed that Mch3β mRNA resulted from two simultaneous alternative splicing events. The first event caused the deletion of nucleotides 488–592 of the Mch3of sequence (SEQ ID NO: 1) due to the use of an alternative splice donor located within the coding region of the 5' exon and an alternative splice acceptor located within the 3' intron. The second splicing event caused an insertion of 74 bp intronic sequence due to the use of an alternative spice donor located within the intron and the normal splice acceptor of the 3' exon. All the alternative splice donor/acceptor sites used in these events conform to the GT/AG rule. As a result of the deletion and insertion, Mch3β cDNA did not maintain the same reading frame as Mch3α after amino acid 148. The new reading frame in Mch3β does not encode a QACRG pentapeptide sequence and it terminates with a TGA stop codon corresponding to bp 837–839 of Mch3β (FIG. 1; SEQ ID NO: 1). Mch3β encodes a protein of 253 amino acids with a predicted molecular mass of ~28 kDa (SEQ ID NO: 4).

In vitro translated Mch3α and Mch35 migrate as 36 and 33 kDA protein products. The smaller translation products seen in the Mch3α and Mch3β translation reactions are probably internally translated products. Although the calculated molecular mass of Mch3β is ~28 kDA, its migration as a 33 kDa indicates posttranslational modification such as phosphorylation. This result is evident from the high number of serine residues in Mch3β sequence that is different from Mch3α and its migration in SDS gels as a fuzzy band rather than a sharp distinct band. The function and activity of Mch3α is discussed further below. However, similar to the alternatively spliced Ich-1 isoform (Ich-1s), (Wang et al., *Cell* 78:739–750 (1994)) Mch3β is thought to be a negative regulator of apoptosis and could inhibit the activity of the parental enzyme by acting as a dominant inhibitor.

Sequence comparison of the predicted full length Mch3α protein sequence shows the highest homology to human CPP32 and Mch2α and the *C. elegans* CED-3 protein. (Fernandes-Alnemri et al., *J. Biol. Chem.* 269:30761–30764 (1994))-Overall, Mch3α protein shares ~53% identity (67% similarity) with CPP32, ~35% identity (56% similarity) with Mch2α and ~33% identity (55% similarity) with CED-3. Mch3α shows less than 30% identity with other family members such as ICE, NEDD/ICH-1, Tx (ICH-2, ICE$_{rel}$-II) or ICE$_{rel}$III. In addition to the conservation of the active site QACRG (SEQ ID NO: 14) pentapeptide the predicted structure of Mch3α appears to be similar to CPP32. CPP32 is cleaved at Asp28 and Asp175 to generate two polypeptides of molecular masses of 17 kDa (p17) and 12 kDa (p12) that form the active CPP32 enzyme complex. Based on the high homology between Mch3α and CPP32, it is likely that the cleavage sites in Mch3α are Asp53 and Asp198 (FIG. 1). Cleavage at these sites would generate two polypeptides equivalent to the p17 and p12 subunits of CPP32. However, there are three potential aspartic acid cleavage sites at positions 15, 20 and 23 that could be used to remove a short propeptide during processing of Mch3α to the active enzyme. In fact, the tetrapeptide DSVD (amino acids 20–23 of Mch3α) (SEQ ID NO: 17) is very similar to the DEVD (SEQ ID NO: 15) tetrapeptide substrate of CPP32. This result indicates that the Mch3α is a substrate for CPP32. In addition, three Asp cleavage sites (Asp193, Asp204 and Asp206) located between the two subunits may serve as potential processing sites to separate the two subunits.

To determine if Mch3 exhibits apoptotic activity, we investigated whether this gene product induces early apoptosis in Sf9 baculovirus cells. Briefly, Sf9 cells were infected with recombinant baculoviruses encoding full length Mch3α, full length CPP32, or truncated Mch3α or CPP32 variants, separately or in various combinations. Cells were then examined microscopically for morphological signs of apoptosis such as blebbing of the cytoplasmic membrane, condensation of nuclear chromatin and release of small apoptotic bodies. In addition the genomic DNA was examined for internucleosomal DNA cleavage.

For the construction of transfer vectors and recombinant baculoviruses, the Mch3 cDNA was amplified by PCR using primers T50-pr3 GCCATAAACTCTTCCTCACTT (SEQ ID NO: 7) and T50-pr4 ATGGCAGATCATCAGGGC (SEQ ID NO: 8) and subcloned into the pBluescript II SK⁻ vector. The Mch3 sequence was then excised with Bam HI and subcloned into a Bam HI cut pVL1393 (Invitrogen, San Diego, Calif.) to generate the pVL-Mch3α transfer vector. The cDNA encoding the p20 and p12 subunits of Mch3 were amplified with PCR using the following primers (p20 subunit; T50-pr4 (SEQ ID NO: 8) and Mch3-p20-TAG-CTAGTCGGCCTGGATGCCATC (SEQ ID NO: 9) and p12 subunit; Mch3-p12-ATG ATGTCGGGGCCCATCAAT-GAC (SEQ ID NO: 10)) and T50-pr9 GACCCATTGCT-TCTCAGC (SEQ ID NO: 11)). The PCR products were then cloned into a Sma I cut pVL1393 to generate pVL-Mch3-p20 and pVL-Mch3-p12 transfer vectors. The recombinant transfer vectors were then used to generate recombinant Baculoviruses as previously described (Summers et al., "Manual of Methods for Baculovirus Vectors and Insert Culture Procedures," *Texas Experimental Station Bulletin No*, 1555 (Texas A&M University, College Station, Tex. (1987); and Alnemri et al., *J. Biol. Chem.* 266:3925–3936 (1991)).

For the induction of apoptosis in Sf9 cells by Mch3α and CPP32. Internucleosomal DNA cleavage was assessed as a characteristic marker. Briefly, total cellular DNA was isolated at 42 h postinfection from Sf9 cells infected with the wild type baculovirus or the recombinant baculoviruses AcNPV-Mch3α or AcNPV-ICE, which have been described previously (Summers et al. and Alnemri et al. supra). The DNA samples were analyzed by electrophoresis in a 1.8% agarose gel containing ethidium bromide.

Expression of full length Mch3α in Sf9 cells caused approximately 50% of the cells to undergo apoptosis by 48 h postinfection which was also manifested by induction of internucleosomal DNA cleavage. This result is consistent with Mch3 being an apoptotic protease since ICE, CPP32 and Mch2α yield similar results. On the other hand, truncated Mch3α (amino acids 1–198) that encodes only the p20 subunit or truncated Mch3α (amino acids 199–303) that encodes only the p12 subunit, were unable to induce apoptosis in Sf9 cells when expressed separately (FIG. 2, columns 1 and 2). However, when these two subunits were coexpressed, ~49% of the cells died by apoptosis (column 3). Similarly, the two subunits of CPP32 were not apoptotic when expressed separately (columns 4 and 5) but were apoptotic when coexpressed together (column 6). The most interesting results were obtained when Mch3-p20 subunit was coexpressed with CPP32-p12 subunit or vice versa (i.e. CPP32-p20 with Mch3-p12). These combinations were able to cause apoptosis in more than 50% of the cells (columns 9 and 10). No significant induction of apoptosis was observed in control cells coexpressing Mch3-p20 and CPP32-p20 together or cells coexpressing Mch3-p12 and CPP32-p12 together (columns 7 and 8). These data indicate that Mch3α and CPP32 can heterodimerize in vivo in eucaryotic cells to form active apoptotic complexes. Such a dimerization now increases the complexity of the apoptotic response in mammalian cells. One interesting observation so far is that all known mammalian Ced3/ICE-like cysteine proteases are expressed in a single cell line namely human Jurkat T-lymphocytes. The ability of different members of the ICE-family such as Mch3 and CPP32 or ICE and Tx to heterodimerize indicates that there may be some overlap in function or subtle differences in specifications that have yet to be characterized.

To further characterize Mch3, the tissue distribution was analyzed by Northern blot analysis of poly A+ RNA isolated from different human tissues. The analysis was performed on Northern blots prepared by Clontech containing 2 µg/lane of poly A+ RNA. Radioactive riboprobe of Mch3α was prepared using a Sma I linearized pBluescript II SK⁻-Mch3α as a substrate for T7 RNA polymerase in the presence of [$\alpha^{32}P$] UTP. The blot was hybridized, washed and then visualized by autoradiography. The results indicate a major 2.4 Kb Mch3 message was detectable in all tissues examined. The lowest expression of Mch3 mRNA was seen in whole brain. Examination of Mch3 mRNA in different regions of the brain also showed low but detectable expression. Similar tissue distribution was also seen with CPP32 mRNA, although the CPP32 message is more abundant than Mch3 message in brain tissues. The size of Mch3 mRNA was consistent with the length of the cloned Mch3α and β cDNAs (FIG. 1; SEQ ID NOS: 1 and 3). Two less abundant messages of (0.8 and 3.3 Kb) were also detectable in some tissues such as the small intestine. The larger message could be an incompletely processed Mch3 RNA or an alternatively spliced Mch3 isoform. The smaller message could be a degradation product or an alternatively spliced Mch3 isoform.

The enzymatic activity of Mch3α was also characterized in vitro. Mch3 was expressed in *E. coli* as a fusion protein with glutathione S-transferase (GST) as described for Mch2α, ICE and CPP32 (See for example, Alnemri et al., *J. Biol. Chem.* 270:4312–4317 (1995)). Two GST-Mch3α expression vectors were constructed and transformed into DH5α bacteria. The Mch3α1 cDNAs were subcloned in-frame into the Bam HI site of the bacterial expression vector pGEX-2T (Pharmacia, Biotech, Inc.) The first construct (Mch3al) contains a PCR generated cDNA that encodes amino acids 1–303 of Mch3α fused to the C-terminus of GST. The second construct (Mch3α2) contains a Bam HI fragment derived from the Mch3 λ library clone that encodes the full length Mch3α and an extra 16 amino acids derived from the 5' nontranslated region fused to the C-terminus of GST. After induction with IPTG, bacterial extracts were prepared from *E. coli* expressing the recombinant fusion proteins. The extracts were adsorbed to glutathione-Sepharose resin, washed several times and then analyzed by SDS-PAGE.

The Mch3α1 preparation contained a major GST-fusion protein that migrated as a ~30 kDa band. On the other hand, the Mch3α2 preparation contains a major GST-fusion protein that migrated as a ~32 kDa band. The GST nonfusion protein control migrated as a ~28 kDa protein These results are consistent with autocatalytic processing and cleavage of GST-Mch3α in bacteria most probably at Asp23 of Mch3α to generate the 30 and 32 kDa GST-prodomain fusion. A minor GST-fusion protein that migrated as a 33 kDa band in Mch3α preparation and as a 35 kDa protein in Mch3α2 preparation was also seen above the major 30 and 32 kDa bands, respectively. These two bands are intermediate cleavage products generated by cleavage at a site C-terminal to Asp23 of Mch3α. This indicates that the final product of Mch3α processing is cleaved at an Asp site C-terminal to Asp23 and is likely to be Asp53.

EXAMPLE II

Kinetic Properties and Enzymatic Activity of Mch3α

This Example characterizes the protease activity and substrate specificity of the apoptotic cysteine protease Mch3.

The kinetic properties of the bacterially expressed recombinant Mch3α and CPP32 were determined using the tetrapeptide substate DEVD-AMC in a continuous fluorometric assay. The DEVD-AMC substrate is the poly(ADP-ribose)polymerase (PARP) cleavage site P1-P4 tetrapeptide (Nicholson et al., *Nature* 376:37–43 (1995)). Briefly, activity of Mch3α and CPP32 was measured using bacterial lysates in ICE buffer (25 mM HEPES, 1 mM EDTA, 5 mM DTT, 0.10% CHAPS, 10% sucrose, pH 7.5) at room temperature (24–25° C.). $K_i$'s were determined from the hydrolysis rate of 50 μM DEVDamc (10 μM for CPP32) in ICE buffer following a 30 min preincubation of the enzyme with inhibitor. Prior to incubation with enzyme, purified crmA was activated by incubation with 5 mM DTT for 10 min at 37° C.

TABLE I

| Parameter | Protease | |
|---|---|---|
| | Mch3 | CPP32 |
| $k_{cat}/K_m$ (DEVDamc, mM$^{-1}$s$^{-1}$) | 11 | 1600 |
| $K_m$ (DEVDamc, μM) | 51 | 13 |
| $k_{cat}/K_m$ (YVADamc, mM$^{-1}$s$^{-1}$) | NA | 0.067 |
| Km (YVADamc, μM) | NA | >500 |
| $K_i$ (DEVDaldehyde, nM) | 1.8 | 0.59 |
| $K_i$ (YVADaldehyde, μM) | >10 | 8.5 |
| $K_i$ (CrmA, μM) | >1 | 0.56 |

Both Mch3α and CPP32 exhibited a Michaelis-Menton kinetics in cleaving this substrate with $K_m$ values of 51 and 13 μM, respectively (Table I). These $K_m$ values and other kinetic parameters are shown above in Table I. For example, the $K_m$ value of recombinant CPP32 (13 μM) was comparable to the $K_m$ value of purified human CPP32 (9.7±1.0 μM) reported recently (Nicholson et al., supra). The peptide aldehyde DEVD-CHO was also a potent inhibitor of both Mch3α and CPP32 at low nM concentrations ($K_{iMCh3}$=1.8 nM and $K_{iCPP32}$=0.59 nM). In contrast, the ICE inhibitor peptide aldehyde YVAD-CHO ($K_{iICE}$=0.76 nM) was a very weak inhibitor of both Mch3α and CPP32 ($K_{iMCh3}$>10 μM and $K_{iCPP32}$=8.5 μM). The ICE inhibitor cowpox serpin, Crm A, similarly was also a very weak inhibitor of Mch3α and CPP32 ($K_{iMch3}$>1 μM and $K_{iCPP32}$=0.56 μM). These data indicate that the two enzymes, Mch3α and CPP32 have similar substrate specificity.

In addition, the high concentration of Crm A required to inhibit either CPP32 or Mch3 indicates that the target of Crm A inhibition in apoptosis is unlikely to be CPP32 or Mch3α. Therefore, Crm A inhibition of apoptosis is likely mediated through ICE or an ICE-related protease and not through Mch3 or CPP32. CPP32 has also been recently reported to be the PARP cleaving enzyme in apoptosis (Nicholson et al., supra, and Tewavi et al., *Cell* 81:1–9 (1995)). However, since our data indicate that Mch3α has a similar substrate specificity towards PARP as CPP32 it is possible that some of this previously reported activity is due to Mch3α. For example, incubation of purified bovine PARP or human Hela nuclei with Mch3α resulted in a complete cleavage of PARP in less than 15 min. A similar activity was also observed with CPP32 and with S/M extracts derived from chicken DU249 cells committed to apoptosis.

Inhibition studies with the serine proteases TLCK and TPCK (N-Tosyl-L-Lysyl chloromethylketone and N-Tosyl-L-phenylalanyl chloromethylketone, respectfully) revealed interesting results. At 1 mM DTT concentration TPCK was able to inhibit both Mch3α and CPP32 PARP cleaving activity. At the same DTT concentration TLCK did not inhibit Mch3α but it did inhibit CPP32 activity. In contrast, at 5 mM DTT concentration both TLCK and TPCK were unable to inhibit either Mch3α or CPP32 activity. These results indicate that the concentration of thiol agents influences significantly the activity of cysteine protease and their sensitivity to some inhibitors such as TLCK and TPCK.

EXAMPLE III

Interrelationship of MCH3α and CPP32

This Example shows that Mch3α is a substrate for CPP32.

The ability of subunits derived from Mch3α to form active complexes with subunits derived from CPP32 raised the possibility that Mch3α was a substrate for CPP32 and vice versa. To test this possibility, a GST-Mch3α and GST-CPP32 fusion proteins were in vitro translated in reticulocyte lysate in the presence of $^{35}$S-methionine. Briefly, Mch3α, Mch3β, GST-Mch3α and GST-CPP32 cDNAs were subcloned into the pBluescript II KS$^+$ plasmid under the T7 promoter These vectors were linearized with the appropriate restriction enzyme and used as template for T7 RNA polymerase. The in vitro synthesized mRNA was then used for in vitro translation with reticulocyte lysates as described previously (Alnemri et al., supra).

Figure 3A:
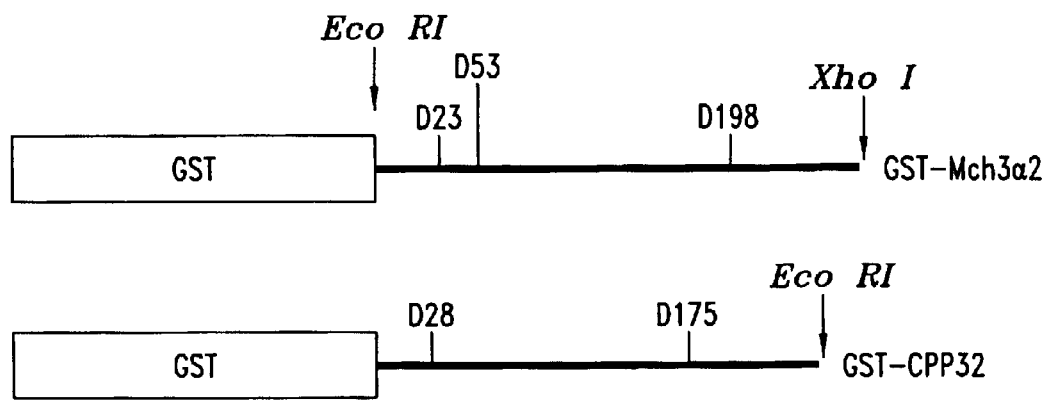
FIG. 3 shows the cleavage of ProMch3α by CPP32.
Figure 3B:
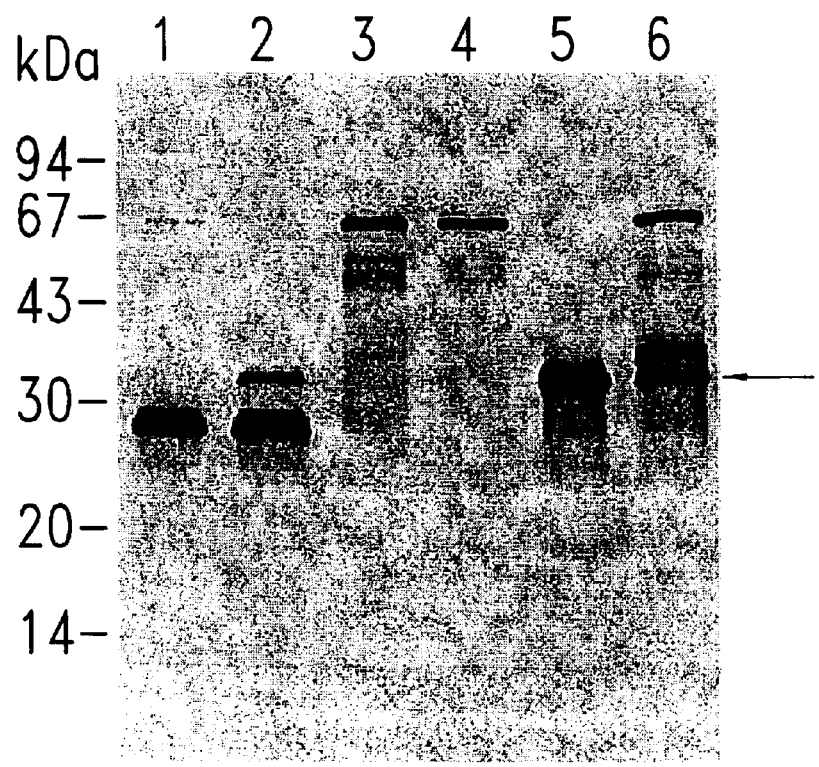

To assess substrate specificity of these proteases, the labeled lysates were incubated with recombinant active CPP32 or Mch3α enzymes (equal DEVD-AMC cleaving activity). After the Incubation period, the cleavage products were immobilized on GST-sepharose, washed several times and analyzed by SDS-PAGE and autoradiography. Schematic diagrams of the vectors are shown in FIG. 3A. The results of the cleavage products indicate that incubation of CPP32 with the in vitro translated GST-Mch3α generated a GST-prodomain cleavage product of molecular mass 32 kDa (FIG. 3B, Lane 5). This band was similar in size and comigrated with the bacterially expressed GST-prodomain. Although Mch3α exhibited significantly less activity than CPP32 towards the in vitro translated GST-Mch3α, a similar cleavage product was observed (FIG. 3B, lane 6). The intermediate 36 kDa minor GST-prodomain cleavage product was also seen in this reaction. No cleavage was observed when CPP32 was incubated with an in vitro translated GST control or when the in vitro translated GST-Mch3α was incubated with buffer (FIG. 3B, lanes 2–4).

Figure 3C:
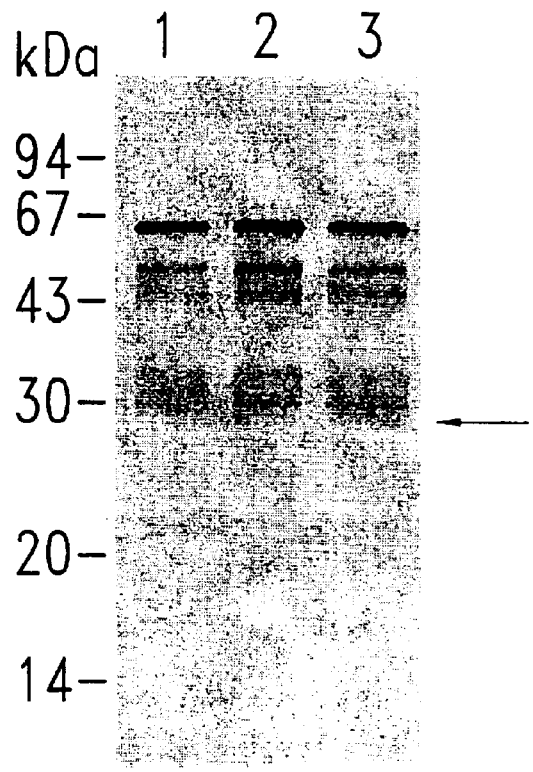

The same experiment was performed with in vitro translated GST-CPP32 (FIG. 3C). In this case, CPP32 showed a very weak activity towards its precursor and generated a faint GST-prodomain band of 30 kDa size as expected from cleavage at Asp28 (lane 3). No cleavage was observed in the buffer control or the Mch3α reaction (FIG. 3C, lanes 1 and 2). Although Mch3α or CPP32 can autoactivate/autoprocess when overexpressed in bacteria, such a process is likely to be regulated in mammalian cells. Therefore, the ability of CPP32 to cleave the Mch3α precursor better than Mch3α itself and the weak activity of CPP32 or Mch3α towards the CPP32 precursor indicates that Mch3α precursor is down stream of CPP32 and that CPP32 is likely dependent on an upstream protease for activation in vivo.

Figure 3D:
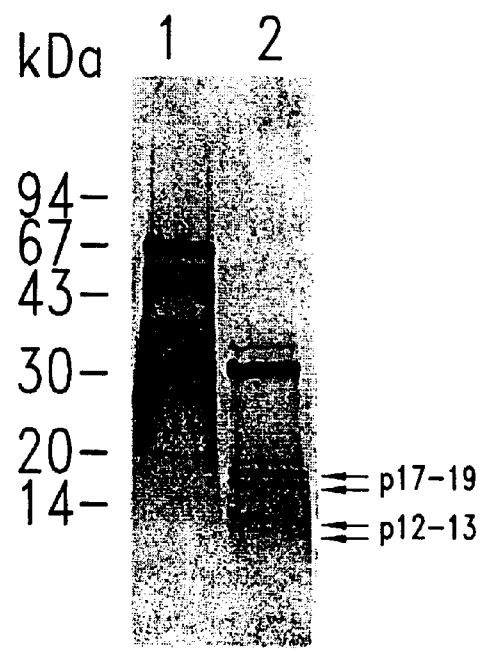

In light of the fact that CPP32 was observed to efficiently cleave the GST-Mch3α precursor, a further purification of the cleavage products from the GST-prodomain was performed and analyzed. Briefly, the $^{35}$S-labeled GST-Mch3α precursor was immobilized on GST-sepharose and washed several times. The resine-GST-Mch3α precursor was incubated with active CPP32 and the soluble products cleaved from the immobilized GST-Mch3α precursor were then analyzed on a 10–20% gradient SDS gel and visualized by autoradiography (FIG. 3D). The three bands that migrate as 17–19 kDa proteins represent the large subunit of Mch3 at different stages of processing. Similarly, the two bands of 12–13 kDa size represent the small subunit of Mch3α. The bands that migrate as 30 and 35 kDa proteins represent Mch3α precursor minus the prodomain.

In conclusion, the Mch3 gene encodes two Mch3 proteins, an active Mch3α and a Mch3ß splice variant with an undetermined activity. Because of the high degree of homology between Mch3 and CPP32 and their ability to heterodimerize to form active heteromeric complexes, the Mch3β variant is likely to function as a dominant inhibitor of both Mch3β and CPP32. The similarity between CPP32 and Mch3α in terms of their kinetic properties and their substrate specificity towards the DEVD peptide and PARP indicates that CPP32 may not be the sole PARP cleaving enzyme in apoptosis. The possibility that Mch3α is down stream of CPP32 suggest that CPP32 might be the PARP cleaving enzyme during the early stages of apoptosis but that Mch3α may be involved in the final stages of PARP cleavage and apoptosis. It therefore appears that activation of the death program in mammalian cells is regulated by multiple pathways and that execution of apoptosis may involve different cascades of cysteine proteases.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. An isolated antibody that specifically binds an Mch3 polypeptide said polypeptide comprising SEQ ID NO:4.

2. The antibody of claim 1, wherein said antibody is a monoclonal antibody.

3. The antibody of claim 1, wherein said antibody is a polyclonal antibody.

* * * * *